United States Patent [19]

Devanathan

[11] Patent Number: 4,902,297
[45] Date of Patent: Feb. 20, 1990

[54] COMPOSITE IMPLANT PROSTHESIS

[75] Inventor: Thirumalai N. C. Devanathan, Warsaw, Ind.

[73] Assignee: Zimmer, Inc., Warsaw, Ind.

[21] Appl. No.: 373,645

[22] Filed: Jun. 21, 1989

Related U.S. Application Data

[63] Continuation of Ser. No. 277,531, Nov. 28, 1988, abandoned, which is a continuation of Ser. No. 835,486, Mar. 3, 1986, abandoned.

[51] Int. Cl.$^4$ .......................... A61F 2/28; A61F 2/32; B05D 3/02; D04C 1/00
[52] U.S. Cl. ........................................ 623/16; 623/23; 428/365; 428/367; 428/375; 428/377; 87/1; 87/6
[58] Field of Search .............................. 623/13, 16–23, 623/66; 428/365, 367, 375, 377; 87/1, 6; 244/133

[56] References Cited

U.S. PATENT DOCUMENTS

| | | | |
|---|---|---|---|
| 2,712,263 | 7/1955 | Crandall | 87/1 |
| 3,893,196 | 2/1975 | Hochman | 3/1.91 |
| 3,936,336 | 2/1976 | Phillips | 428/367 X |
| 4,312,917 | 1/1982 | Hawley | 428/375 |
| 4,536,438 | 8/1985 | Bishop et al. | 428/367 X |
| 4,750,905 | 6/1988 | Koeneman et al. | 623/16 |

OTHER PUBLICATIONS

Applications of Advanced Composites in Orthopaedic Implants, Kenneth R. St. John, Chapter 37 Hexcel Corporation (undated).
Absorbable Polymer-Parsons, Alexander and Weiss, Composites for Orthopaedics Report (undated).
Carbon Fiber-Reinforced Carbon as a Potential Implant Material, Adams & Williams, 1978, pp. 35–42, Journal of Biomedical Materials Research vol. 12, 35–42 (1978).
Method for Development of a Composite Material, Hip Repl., Ainsworth, Tarr, Claes.

Primary Examiner—Alan W. Cannon
Attorney, Agent, or Firm—Paul D. Schoenle

[57] ABSTRACT

A composite implant prosthesis comprising a core constructed from a plurality of carbon fibers, a first casing formed from a braided sheath of carbon fibers and a second casing enclosing the core and first casing to define an outer surface contour for the composite implant prosthesis. The method for constructing the composite implant prosthesis includes the steps of pultruding the core from a polymer impregnated tow, braiding the first casing to the pultruded core and applying the second casing thereto. The pultruding and braiding steps are performed in a continuous process while the second casing is applied to a discrete element formed from the core.

2 Claims, 1 Drawing Sheet

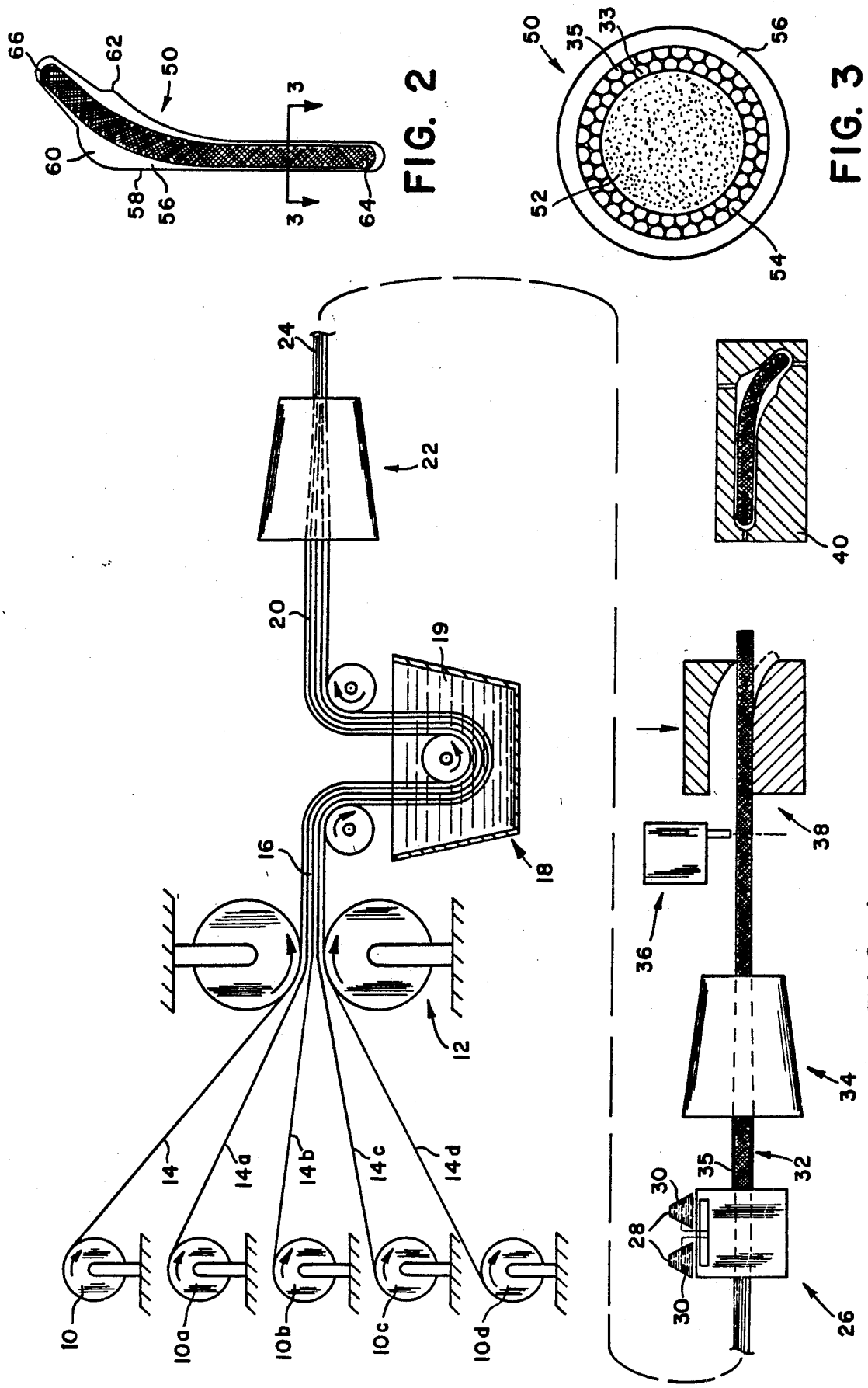

COMPOSITE IMPLANT PROSTHESIS

This application is a continuation of application Ser. No. 07/277,531 filed on Nov. 28, 1988 now abandoned, which is a continuation of Application Ser. No. 06/835,486 filed on Mar. 3,1986, now abandoned.

The invention relates to a composite implant prosthesis and the method of manufacture for the composite implant prosthesis.

Heretofore, composite implants have been formed from a laminated construction which requires machining and material removal in order to form the final contour associated with the implant prosthesis. Carbon fibers and polysulfone have been formed in a laminated construction as a solid block and subject to machining. The machining step is believed to be expensive and the interface between the polysulfone and the carbon fibers is exposed to the environment so that degradation of this interface is possible.

With the present invention it is possible to use a continuous process, as opposed to a batch process where the implant starts out as an individual component, so that material is not wasted due to machining and the speed of production is faster. In addition, it is believed that the continuous process described hereinafter generates a Plurality of composite implant Prostheses which is uniform from part to part.

The invention comprises of a composite implant prosthesis with a core formed by a Plurality of substantially unidirectional strands of fiber, an inner casing material substantially enclosing the core and an outer casing defining an outer surface contour for the composite implant Prosthesis. In a preferred embodiment, a Plurality of strands of carbon fiber are disposed within the core to extend in a unidirection. The inner casing braided to the core is formed by strands of carbon fiber that are circumferentially applied to the core at about a ±45° angle relative unidirectional axis and the outer casing defines an irregular dimensional Pattern to accommodate a desired contour for the outer surface which differs from the contour of the braided core. A method for constructing the composite implant Prosthesis includes the steps of: (a) impregnating the strands of fiber with a polymer; (b) forming a unidirectional core using a continuous process such as pultrusion to pull strands of fiber and polymer through several work stations; (c) braiding an outer layer of Polymer imPregnated fiber over the core; (d) consolidating the outer layer with the core by application of heat and Pressure; (e) bending the core to a required geometry; and (f) applying an outer layer of Polymer to obtain a final envelope geometry for the composite implant prosthesis.

It is an advantage of the present invention that a composite implant prosthesis can be produced in a substantially continuous process so that construction time is minimal. Also, each composite implant prosthesis constructed in this manner will be substantially uniform so that variations between individual prostheses will be minimal.

In the drawings

FIG. 1 is a schematic illustration of the Process contemplated with the present invention.

FIG. 2 is a side view of the composite implant Prosthesis constructed in accordance with the process of FIG. 1.

FIG. 3 is a cross sectional view taken along line 3—3 of FIG. 2.

Turning to FIG. 1, a plurality of spools 10-10d are disposed relative to a pulley or nozzle 12 such that strands of carbon fiber 14-14d carried by each spool 10-10d, respectively, are readily pulled through the pulley 12. The Pulley 12 gathers the plurality of strands of carbon fiber to form a loosely gathered core of fiber reinforcing tow. The loosely gathered core 16 is fed into a heated bath 18 filled with a polymer 19 such as Polysulfone in a molten state. The hot polymer is impregnated into the loosely gathered core to substantially contact all of the strands of carbon fiber and eliminate pockets or cavities of air. Upon leaving the heated bath, the impregnated tow is flattened before cooling. The polymer impregnated tows 20 are pulled through a pultrusion die 22 to generate a substantially rigid core 24 of lesser diameter than the polymer impregnated tow bundle 20. The pultrusion die 22 includes a series of reducing dies (not shown) for simultaneous application of heat and pressure. When the impregnated core 20 is pulled through the series of reducing dies, the polymer 19 and strands of carbon fiber 14 are melted together to form a rigid core 24 which has substantially uniform fiber/polymer content throughout the entire connection of the rigid core 24. With the rigid core 24 acting as a mandrel, a braider 26 carrying a plurality of spools, shown schematically at 28 with strands of carbon fiber 30, braids a sheath 32 over the rigid core 24. The braided sheath 32 is applied in two layers with a first layer 33, see FIG. 3, adjacent the rigid core 24 and a second layer 35, see FIG. 3, wrapped over the first layer 33. A second pultrusion die 34 pulls the braided sheath 32 and core from the braider 26 through a series of reducing dies associated with pultrusion die 34 in order to partially melt the braided sheath 32 into the polymer impregnated carbon fiber core 24 and form an outer diameter dimension. As a result a Portion of the sheath 32 is integrated with the core to securely fasten the remaining portion of the sheath thereto. Since individual strands of carbon fiber 30 are discernable after pultrusion through the pultrusion die 34, these remaining strands impart torsional stability to the sheathed core and create a porous-like outer surface. As the partially sheathed core exits the second Pultrusion die 34, it is placed in a forming press 38 where heat and pressure are used to form or bend the partially sheathed core as desired. In the preferred embodiment a bend is imparted at a proximal end to define a hip prosthesis. After the bend is imparted, a cutter 36 is activated to cut discrete elements from the continuous rod. From the forming press 38, the discrete element is transferred to a mold 40 where a polymer, such as chopped fiber reinforced polysulfone, is injection molded over the outer surface of the discrete element in intimate contact with the porous-like surface of the braided sheath 32 to form an outer surface contour for the hip prosthesis and to enclose the partially sheathed core.

As shown in FIGS. 2 and 3, the composite hip prosthesis 50 constructed in accordance with the above-described Process includes a carbon fiber/polymer core 52, a first casing 54 formed by the braided sheath which has been Partially imbedded into the core 52, and a second casing 56 formed by injection molded Polysulfone or other suitable polymer. In the Preferred embodiment, the radial dimension of the core is about 0.212 inches (5.4 mm), the radial dimension of the first casing or braided sheath is about 0.025 inches 0.64 mm), and the radial dimension of the second casing is about 0.060 inches (1.52 mm) at a distal end only. With the core subjected to a substantial portion of the load applied to the composite hip prosthesis it is possible to provide an irregular pattern for the second casing to define an outer surface contour 58 that fits into a bone cavity. As shown in FIG. 2, the second casing 56 increases in radial dimension at the proximal end to form a greater trochanter 60 on one side and a lesser trochanter 62 on the other side. Although the radial dimension of the second casing 56 varies over the length of the composite hip prosthesis 50, the core 52 with its braided sheath 54 retains a constant radial dimension from a distal end 64 to a proximal end 66.

As mentioned earlier, the core 52 is a unidirectional carbon fiber/polymer composite rod. The braid applied by the braider 26 also comprises tows or strands of carbon fiber With polysulfone fiber coupled thereto in weight ratios of substantially 60% carbon and 40% polysulfone, which is also the weight ratio of the core 52. The outer casing comprises of chopped fiber-reinforced polysulfone polymer so that the polysulfone polymer is incorporated in the core, the sheath and the second casing.

In a first alternative, the reinforcing fiber and matrix polymer can be combined in a dry blending process where the polymer is converted to a multifilament tow comprising individual filaments with a diameter less than 10 micrometers. This polymer tow is then combined with a tow of reinforcing fibers, in the appropriate weight ratio to yield a single tow of reinforcing and matrix fibers. The two tows are combined by blowing air to create intermingling, such that each reinforcing fiber is surrounded by matrix fibers. This yields a final composite material with a uniform matrix/fiber distribution across the entire cross-section.

In a second alternative, referred to as powder coating, a conductive reinforcing fiber is passed through a fluidized bed of matrix polymer powder. A current is passed through the fiber to heat it resistively, or the same effect can also be achieved by electrostatic deposition. The tacky, polymer coated fiber is then flattened between a Pair of rollers or pultruded to yield a uniform fiber/polymer tow. Next a braided sheath is applied in the same manner mentioned earlier to provide an angle-ply of reinforcing fibers. The angular orientation is about ±45° relative to a longitudinal axis for the core, preferably, the braided layer is polymer rich to avoid delamination under cyclic loading condition. This can be achieved by using a preimpregnated fiber tow from the solution, electrostatic or resistance heating, or using a pultruded rod with a polymer rich outer surface. Another pultrusion step integrally binds the braided sheath to the outer surface of the core, and a thermoform step imparts the final curved shape by a pair of matching dies so that a cutter will separate discrete elements from the continuous rod for application of the outer casing of chopped fiber reinforced matrix polymer.

I claim:
1. A composite implant prosthesis comprising a core formed by a plurality of substantially unidirectional strands of fiber, each fiber extending substantially over the complete length of the core, an inner casing defined by a braided material enclosing the core over its entire length to form a rigid member, and an outer casing enclosing the inner casing and defining an outer surface contour for the composite implant prosthesis, the core and the inner casing defining a substantially uniform width from one end to the other end while the outer casing defines an irregular width from the one end to the other end to accommodate disposition of the prosthesis adjacent a bone.

2. The composite implant prosthesis of claim 1 in which the braided material of the inner casing is partially embedded and integrated into the core to enhance fixation therewith when the inner casing is secured to the cord.

* * * * *